(12) United States Patent
Hok et al.

(10) Patent No.: US 11,391,724 B2
(45) Date of Patent: Jul. 19, 2022

(54) BREATH TEST SYSTEM

(71) Applicant: Automotive Coalition for Traffic Safety, Inc., Washington, DC (US)

(72) Inventors: Bertil Hok, Vasteras (SE); Lars Tenerz, Uppsala (SE); Leif Smith, Uppsala (SE); Annika Kaisdotter Andersson, Vasteras (SE)

(73) Assignee: Automotive Coalition For Traffic Safety, Inc., Leesburg, VA (US)

( * ) Notice: Subject to any disclaimer, the term of this patent is extended or adjusted under 35 U.S.C. 154(b) by 0 days.

(21) Appl. No.: 14/421,371

(22) PCT Filed: Aug. 23, 2013

(86) PCT No.: PCT/SE2013/050991
§ 371 (c)(1),
(2) Date: Feb. 12, 2015

(87) PCT Pub. No.: WO2014/031072
PCT Pub. Date: Feb. 27, 2014

(65) Prior Publication Data
US 2015/0219620 A1    Aug. 6, 2015

(30) Foreign Application Priority Data
Aug. 24, 2012   (SE) .................... 1250954-3

(51) Int. Cl.
*G01N 33/497*   (2006.01)
*G01N 21/3504*  (2014.01)
(Continued)

(52) U.S. Cl.
CPC ....... *G01N 33/4972* (2013.01); *A61B 5/0059* (2013.01); *A61B 5/082* (2013.01);
(Continued)

(58) Field of Classification Search
CPC ....... G01N 33/4972; G01N 2001/2244; B60K 28/06
See application file for complete search history.

(56) References Cited

U.S. PATENT DOCUMENTS

| 3,283,563 A | 11/1966 | Turner et al. |
| 3,301,482 A | 1/1967 | Bullen |

(Continued)

FOREIGN PATENT DOCUMENTS

| CN | 1586944 | 3/2005 |
| CN | 101292158 | 10/2008 |

(Continued)

OTHER PUBLICATIONS

Giebel, Brian M., Thesis and Dissertation, "Advancement and Application of Gas Chromatography Isotope Ratio Mass Spectrometry Techniques for Atmospheric Trace Gas Analysis," Published 2011, 252 total pages.

(Continued)

*Primary Examiner* — Lisa M Caputo
*Assistant Examiner* — Alex T Devito
(74) *Attorney, Agent, or Firm* — Pandiscio & Pandiscio

(57) ABSTRACT

A breath test system is provided comprising a sensor unit configured to sense the presence or concentration of a volatile substance present in air flowing through a predefined inlet area, and generate a signal corresponding to the concentration of said substance. Also provided is an apparatus configured to detect the presence of a person in the vicinity of said input area, and registering said presence, and configured to respond by delivering an output. This apparatus includes a unit configured to call for immediate attention of said person, and upon registration of the presence of said person, provide instructions to said person to direct an expiratory air flow towards said inlet area. An analyzer to (Continued)

determine breath substance concentration of said person is also provided, the determination based on said signal corresponding to the substance concentration.

17 Claims, 4 Drawing Sheets

(51) Int. Cl.
    *A61B 5/00*            (2006.01)
    *A61B 5/08*            (2006.01)
    *A61B 5/083*           (2006.01)
    *G01N 1/22*            (2006.01)
    *B60K 28/06*           (2006.01)

(52) U.S. Cl.
    CPC .......... *A61B 5/0836* (2013.01); *A61B 5/4845* (2013.01); *G01N 21/3504* (2013.01); *B60K 28/06* (2013.01); *G01N 2001/2244* (2013.01)

(56) References Cited

U.S. PATENT DOCUMENTS

| | | | |
|---|---|---|---|
| 3,780,311 A | 12/1973 | Brown | |
| 3,792,272 A * | 2/1974 | Harte | G01N 21/3504 250/343 |
| 3,792,351 A * | 2/1974 | Ireland | G01R 23/07 324/76.51 |
| 3,830,630 A | 8/1974 | Kiefer et al. | |
| 3,897,659 A * | 8/1975 | Henry | B24B 47/20 451/26 |
| 4,090,078 A * | 5/1978 | Heim | G01N 33/4972 250/343 |
| 4,294,327 A | 10/1981 | Howard | |
| 4,535,620 A | 8/1985 | Cunningham | |
| 4,678,057 A * | 7/1987 | Elfman | B60K 28/063 180/272 |
| 4,749,553 A | 6/1988 | Lopez et al. | |
| 4,843,377 A | 6/1989 | Fuller et al. | |
| 4,868,545 A | 9/1989 | Jones | |
| 4,916,435 A * | 4/1990 | Fuller | G07C 9/00103 340/573.4 |
| 4,975,581 A | 12/1990 | Robinson et al. | |
| 5,006,315 A | 4/1991 | Maroulis et al. | |
| 5,303,575 A | 4/1994 | Brown et al. | |
| 5,426,415 A | 6/1995 | Prachar et al. | |
| 5,458,853 A | 10/1995 | Porter et al. | |
| 5,485,850 A | 1/1996 | Dietz | |
| 5,544,276 A | 8/1996 | Loux et al. | |
| 5,652,398 A | 7/1997 | Johnson | |
| 5,655,530 A | 8/1997 | Messerschmidt | |
| 5,693,944 A * | 12/1997 | Rich | G01N 21/0303 250/343 |
| 5,731,581 A | 3/1998 | Fischer et al. | |
| 5,746,973 A | 5/1998 | Naraghi | |
| 5,823,951 A | 10/1998 | Messerschmidt | |
| 5,830,112 A | 11/1998 | Wang et al. | |
| 5,877,345 A | 3/1999 | Bauer et al. | |
| 5,906,203 A | 5/1999 | Klockseth et al. | |
| 5,955,886 A | 9/1999 | Cohen et al. | |
| 5,971,937 A | 10/1999 | Ekstrom | |
| 6,123,674 A | 9/2000 | Rich | |
| 6,129,680 A | 10/2000 | Mottram | |
| 6,142,951 A | 11/2000 | Park | |
| 6,152,876 A | 11/2000 | Robinson et al. | |
| 6,157,041 A | 12/2000 | Thomas et al. | |
| 6,229,908 B1 | 5/2001 | Edmonds et al. | |
| 6,266,353 B1 | 7/2001 | Freitas et al. | |
| 6,441,388 B1 | 8/2002 | Thomas et al. | |
| 6,468,222 B1 | 10/2002 | Mault et al. | |
| 6,488,635 B1 | 12/2002 | Mottram | |
| 6,528,809 B1 | 3/2003 | Thomas et al. | |
| 6,608,399 B2 | 8/2003 | McConnell et al. | |
| 6,622,032 B1 | 9/2003 | Robinson et al. | |
| 6,684,099 B2 | 1/2004 | Ridder et al. | |
| 6,726,636 B2 | 4/2004 | Der Ghazarian et al. | |
| 6,748,301 B1 | 6/2004 | Ryu | |
| 6,794,988 B1 | 9/2004 | Weiss et al. | |
| 6,862,091 B2 | 3/2005 | Johnson | |
| 6,983,176 B2 | 1/2006 | Gardner et al. | |
| 7,016,713 B2 | 3/2006 | Gardner et al. | |
| 7,092,832 B2 | 8/2006 | Brown | |
| 7,098,037 B2 | 8/2006 | Haas et al. | |
| 7,173,524 B2 | 2/2007 | Ponziani | |
| 7,202,091 B2 | 4/2007 | Jones et al. | |
| 7,386,152 B2 | 6/2008 | Rowe et al. | |
| 7,446,878 B2 | 11/2008 | Ridder et al. | |
| 7,671,752 B2 | 3/2010 | Sofer | |
| 7,736,903 B2 | 6/2010 | Lambert et al. | |
| 7,764,982 B2 | 7/2010 | Dalke et al. | |
| 7,848,605 B2 | 12/2010 | Ridder et al. | |
| 7,855,027 B2 | 12/2010 | Bayer et al. | |
| 7,993,281 B2 | 8/2011 | Stock et al. | |
| 8,183,527 B2 | 5/2012 | Taguchi et al. | |
| 8,306,595 B2 | 11/2012 | Osaki et al. | |
| 8,469,134 B2 | 6/2013 | Osaki et al. | |
| 8,605,959 B2 | 12/2013 | Kangas | |
| 8,773,390 B1 | 7/2014 | Clark | |
| 9,068,885 B2 | 6/2015 | Kluczynski et al. | |
| 9,073,431 B2 | 7/2015 | Takahashi | |
| 9,163,718 B2 | 10/2015 | Nelson | |
| 9,758,039 B2 | 9/2017 | Hannon | |
| 9,823,237 B2 | 11/2017 | Martin et al. | |
| 10,151,744 B2 | 12/2018 | Hok et al. | |
| 2002/0084130 A1 | 7/2002 | Der Ghazarian et al. | |
| 2002/0140289 A1* | 10/2002 | McConnell | B60R 11/02 307/10.1 |
| 2003/0039299 A1 | 2/2003 | Horovitz | |
| 2003/0048000 A1 | 3/2003 | Harter | |
| 2003/0085284 A1 | 5/2003 | Bremer et al. | |
| 2004/0093957 A1 | 5/2004 | Buess et al. | |
| 2004/0260194 A1 | 12/2004 | Bayer | |
| 2005/0241871 A1* | 11/2005 | Stewart | G01N 33/4972 180/272 |
| 2006/0058697 A1 | 3/2006 | Mochizuki et al. | |
| 2006/0153740 A1* | 7/2006 | Sultan | B60K 28/06 422/88 |
| 2006/0154377 A1 | 7/2006 | Lambert et al. | |
| 2006/0167349 A1 | 7/2006 | Gardner et al. | |
| 2006/0206034 A1 | 9/2006 | Stock et al. | |
| 2006/0210120 A1 | 9/2006 | Rowe et al. | |
| 2006/0253711 A1 | 11/2006 | Kallmann | |
| 2007/0077176 A1 | 4/2007 | Lambert et al. | |
| 2007/0142720 A1 | 6/2007 | Ridder et al. | |
| 2007/0144812 A1 | 6/2007 | Stewart et al. | |
| 2007/0245801 A1 | 10/2007 | Stock | |
| 2008/0006077 A1 | 1/2008 | Crabtree et al. | |
| 2008/0045806 A1 | 2/2008 | Keppler | |
| 2008/0061238 A1* | 3/2008 | Hok | G01N 21/3504 250/340 |
| 2008/0107309 A1 | 5/2008 | Carni | |
| 2008/0171947 A1 | 7/2008 | Ruffert | |
| 2008/0228098 A1 | 9/2008 | Popov et al. | |
| 2008/0252412 A1 | 10/2008 | Larsson et al. | |
| 2008/0319286 A1 | 12/2008 | Ridder et al. | |
| 2009/0007634 A1 | 1/2009 | Mitchell | |
| 2009/0039267 A1 | 2/2009 | Arndt et al. | |
| 2009/0087920 A1 | 4/2009 | Pettersson et al. | |
| 2009/0248260 A1 | 10/2009 | Flanagan | |
| 2009/0293589 A1 | 12/2009 | Freund et al. | |
| 2010/0010325 A1 | 1/2010 | Ridder et al. | |
| 2010/0028210 A1 | 2/2010 | Ozaki et al. | |
| 2010/0031718 A1 | 2/2010 | Heil | |
| 2010/0036592 A1 | 2/2010 | Osaki et al. | |
| 2010/0188232 A1* | 7/2010 | Lambert | G01N 21/3504 340/573.1 |
| 2010/0268425 A1 | 10/2010 | Pettersson et al. | |
| 2010/0327167 A1 | 12/2010 | Koop et al. | |
| 2011/0178420 A1 | 7/2011 | Ridder et al. | |
| 2011/0283770 A1 | 11/2011 | Hok | |
| 2011/0302992 A1 | 12/2011 | Robbins et al. | |
| 2011/0308297 A1 | 12/2011 | Tsuzuki et al. | |
| 2011/0309932 A1 | 12/2011 | Arringdale et al. | |

(56) References Cited

U.S. PATENT DOCUMENTS

| | | |
|---|---|---|
| 2012/0112879 A1 | 5/2012 | Ekchian et al. |
| 2013/0110311 A1 | 5/2013 | Ver Steeg |
| 2014/0002237 A1 | 1/2014 | Infante et al. |
| 2014/0156149 A1 | 6/2014 | Feit |
| 2014/0260537 A1 | 9/2014 | Nash |
| 2014/0318293 A1 | 10/2014 | Nelson |
| 2015/0066238 A1 | 3/2015 | Todd et al. |
| 2015/0219620 A1 | 8/2015 | Hok et al. |
| 2015/0233897 A1 | 8/2015 | Hok |
| 2016/0356764 A1 | 12/2016 | Martin et al. |
| 2017/0050518 A1 | 2/2017 | Steeg et al. |
| 2017/0074857 A1 | 3/2017 | Dennis et al. |
| 2017/0274768 A1 | 9/2017 | Hök et al. |

FOREIGN PATENT DOCUMENTS

| | | |
|---|---|---|
| CN | 101334399 A | 12/2008 |
| CN | 101631497 | 1/2010 |
| CN | 102316801 A | 1/2012 |
| CN | 101354394 | 10/2012 |
| DE | 4127599 A1 | 2/1993 |
| DE | 198 11 872 | 8/1999 |
| DE | 199 38 064 | 8/2000 |
| DE | 101 57 907 | 6/2003 |
| DE | 102006018970 B3 | 5/2007 |
| DE | 102011106410 | 8/2012 |
| EP | 0752584 | 1/1997 |
| EP | 0 791 899 | 8/1997 |
| EP | 1441212 | 7/2004 |
| EP | 1688741 | 8/2006 |
| GB | 2431470 | 4/2007 |
| GB | 2442980 | 4/2008 |
| JP | 11-104112 | 4/1999 |
| JP | 2004-245799 | 9/2004 |
| JP | 2005-157599 | 6/2005 |
| JP | 2006-98058 | 4/2006 |
| JP | 2007-147592 | 6/2007 |
| JP | 2008-253455 | 10/2008 |
| JP | 2008-291710 | 12/2008 |
| JP | 2008-302915 | 12/2008 |
| JP | 2008-308037 | 12/2008 |
| JP | 2009-257768 | 11/2009 |
| JP | 2010-139319 | 6/2010 |
| JP | 2011-153956 | 8/2011 |
| JP | 2012-198648 | 10/2012 |
| SE | 536782 | 8/2014 |
| SE | 536784 | 8/2014 |
| WO | WO 92/22813 | 12/1992 |
| WO | WO 95/26889 | 10/1995 |
| WO | WO97/000443 | 1/1997 |
| WO | WO 98/20346 | 5/1998 |
| WO | WO 01/08554 | 2/2001 |
| WO | WO 2001/008554 | 2/2001 |
| WO | WO-2004090786 | 10/2004 |
| WO | WO 2007/046745 | 4/2007 |
| WO | WO 2008/108714 | 9/2008 |
| WO | WO 2009/048809 | 4/2009 |
| WO | WO 2010/085716 | 7/2010 |
| WO | WO 2010/093317 | 8/2010 |
| WO | WO12/064252 | 5/2012 |
| WO | WO 2013/081519 | 6/2013 |
| WO | WO 2014/031071 | 2/2014 |
| WO | WO 2014/031072 | 2/2014 |
| WO | WO 2016/195803 | 12/2016 |
| WO | WO 2017/164953 | 9/2017 |

OTHER PUBLICATIONS

Talbert, Bruce, et al., "A Study of Regulators for Delivering Gases Containing Low Concentrations of Hydrogen Sulfide," LCGC North America, 22(6):562, 564, 567-568 (2004).

Extended European Search Report EP 13 83 1692 dated Jul. 13, 2015.

Extended European Search Report EP 13 83 0956 dated Jul. 13, 2015.

International Search Report dated Feb. 3, 2014 for PCT/SE2013/050991.

Dhokalia et al., Resting End-Tidal 002 Association With Age, Gender, and Personality, Psychosomatic Medicine, vol. 60, 1998, pp. 33-37.

International Search Report dated Jan. 31, 2014 for PCT/SE2013/050990.

Lambert et al., Passive Sensing of Driver Intoxication, SAE Technical Paper 2006-01-1321, 2006, SAE International.

Blinco, L. J. et al., The Economic and Societal Impact of Motor Vehicle Crashes, 2010 (Revised), National Highway Traffic Safety Administration, May 2015 (Revised), DOT HS 812 013.

Traffic Safety Facts, 2013 Data: Alcohol-Impaired Driving, National Highway Traffic Safety Administration, Dec. 2014, DOT HS 812 102.

\* cited by examiner

BREATH TEST SYSTEM

CROSS-REFERENCE TO RELATED APPLICATIONS

This application is a national stage application under 35 U.S.C. § 371 of International Application No. PCT/SE013/050991, filed Aug. 23, 2013, which claims priority from Swedish Application 1250954-3, filed Aug. 24, 2012. The contents and disclosures of each of those applications are incorporated by reference herein in their entity. International Application No. PCT/SE2013/050991 was published under PCT Article 21(2) in English.

This invention is concerned with a system for the unsupervised sensing the presence/concentration of substances, such as ethyl alcohol, within the expired breath of a person.

BACKGROUND OF THE INVENTION

Breath Alcohol Concentration (BrAC) is related to Blood Alcohol Concentration (BAC) by the approximate relation BrAC[mg/l]=0.5*BAC[mg/g]. Other substances will have different coefficients.

Supervised breath tests according to the state of the art are being performed by the police in order to prevent drunk driving. For the same purpose, unsupervised tests using alcolocks in vehicles are also being increasingly used. Sensor technologies include catalytic semiconductors, fuel cells and infrared spectroscopy. Performance with respect to accuracy, specificity, environmental immunity, and response time, is highly variable between different devices available on the market. Devices for breath test include sensor elements providing a signal representing BrAC after taking a deep breath, and emptying the airways via a tight-fitting mouthpiece, which for hygienic reasons has to be a separate, disposable item. In order to ensure a correct determination, the test person is required to deliver a forced expiration at almost full vital capacity. This requires a substantial effort, especially for persons with limited respiratory capacity. The handling of mouthpieces is costly, time-consuming and represents an undesired source of error due to water condensation.

The basic techniques of breath analysis were developed during the second half of the 20th century. More recently, a movement towards less obtrusive means for breath test has been noted. Olsson et al (WO 98/20346) disclosed a system solution in which accurate measurements could be performed without a mouthpiece using water vapor as a tracer gas. Lopez (U.S. Pat. No. 5,458,853) reported another approach, using ultrasound to correct for the dependence on distance between the device and the user's mouth. Hö k et al (GB 2431470) disclosed a system solution using carbon dioxide ($CO_2$) as a tracer gas, combined with a simple algorithm for correction of a diluted breath sample. Still another approach was reported by Lambert et al (SAE World Congress Apr. 3-6, 2006). The air within a vehicle cabin was monitored, and an alcohol adsorbing material was used to accumulate the sample to enhance resolution. Again, $CO_2$ was used as a tracer gas.

SUMMARY OF THE INVENTION

A specific object of the present invention is to reduce the effort required by the person to be tested to a minimum, without compromising reliability. Other objects are to reduce the total time required for a breath test, and that the system is self-instructive even for an inexperienced person.

The present invention is based on a few critical elements which in combination will provide the necessary characteristics. First, there is provided a sensor unit providing a signal corresponding to the instantaneous alcohol concentration of air flowing through a predefined inlet area. A predefined inlet area is one or several openings, allowing air to be continuously flowing from the inlet area to the sensor. Second, there is provided an apparatus responsive of the presence of a person at a position in the vicinity of the sensor inlet area, and also including a unit for calling for and directing the immediate attention of the person, and of providing instruction to direct expiratory air flow towards the inlet area. This directed breath is a deliberate act by the person. Third, an analyzer is included for the determination of breath alcohol concentration of said person based on the sensor signal.

The combined function of the basic elements is necessary and sufficient for breath tests of experienced users to be effortlessly performed within 2-3 seconds at full privacy, without a mouthpiece, and without interfering with normal activities, such as on-going conversation. The inexperienced user is guided by automatically communicated instructions to successful completion of the test.

The present invention allows breath tests to be performed in a variety of circumstances which have hitherto been inaccessible. The improved user friendliness combined with the possibility of vehicle integration may be an important step towards preventing drunk driving on a much larger scale than with products available at the present. This is believed necessary to reduce the high mortality of alcohol related traffic accidents. Other promising application areas are sobriety control of staff with critical tasks, and of audience arriving at an arena. It may also be used in various self test scenarios, e.g. in the treatment of alcoholics. The possibility of unobtrusive breath tests is expected to become important for diagnostic purposes in emergency medicine. For this purpose, a large number of volatile substances are of interest in addition to ethyl alcohol.

In view of the shortcomings of prior art systems, the inventors have devised a novel system.

Thus, claim 1 defines a breath test system, including a sensor unit (5) configured to sense the presence or concentration of a volatile substance, present in air flowing through a predefined inlet area (4), and to generate a signal corresponding to the concentration of said substance; an apparatus (2, 3) configured to detect the presence of a person at a position in the vicinity of said input area, and having means for registering said presence, and further configured to respond to said presence by delivering an output, said apparatus including a unit configured to call for immediate attention of said person, upon said registration of the presence of said person; and a unit configured to provide instructions to said person to direct an expiratory air flow towards said inlet area (4); an analyzer (10) for the determination of breath substance concentration of said person, the determination being based on said signal corresponding to the substance concentration.

The main advantage of the system is that it is unobtrusive, i.e. it does not unduly interfere with the person subjected to the use of the system.

BRIEF DESCRIPTION OF THE DRAWINGS

The invention will now be described below with reference to the drawings in which.

DETAILED DESCRIPTION

The present invention involves both physical attributes and functional characteristics, as evident both in the enclosed claims and the detailed description.

Figure 1:
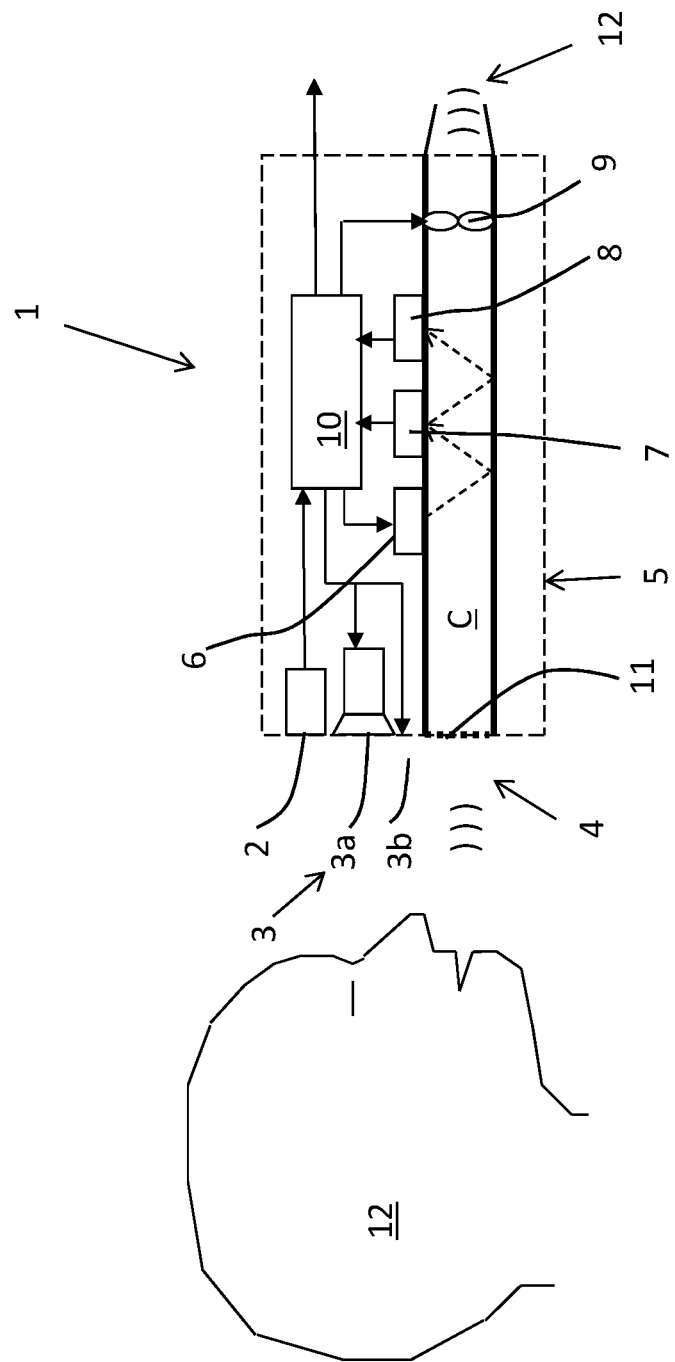
FIG. 1 shows a schematic drawing of the system according to one embodiment.

FIG. 1 is a schematic drawing (not to scale) of one embodiment of the system 1 according to the invention. The system 1 may be built into a separate physical enclosure, or being part of inventories, e.g. in a vehicle cabin. A test person 12 is shown positioned in the vicinity of an inlet area 4 of the sensor unit 5, equipped with a sensor element 8 generating a signal corresponding to the ethyl alcohol concentration of the air flowing through the inlet area 4. Means for active transport of air through the sensor unit 5 is provided by a fan or pump 9, preferably including means for controlling the volume flow. The inlet area 4 constitutes one or several openings, into which air can be freely flowing, or driven by the fan 9. Preferably, a particle filter 11 e.g. made from porous material is included in the inlet area 4. This prevents particles and aerosols from contaminating the sensor unit 5 while not impeding the air flow to any significant degree. When the person 12 is directing expiratory air towards the inlet area 4 from a distance not exceeding 50 cm, the air flowing through the sensor unit 5 will consist of a mixture of ambient and expiratory air from the person 12.

As already explained in the background, a central characteristic of the present system is to obtain cooperation with the person 11 during a short moment of time. The apparatus configured for achieving this includes means for registration 2 of the presence of a person 12 at a position in the vicinity of the inlet area 4, and an audiovisual unit 3. The implementation of the means of registration 2 is highly depending on the actual application and could include a microswitch indicating door opening/closure, microphone, camera, contactless detector using ultrasound or infrared radiation, force sensor responding to the weight of the person. It may include means for identification of the person by voice control, image analysis, bar-code reading, or biometric analysis. The audiovisual unit 3 preferably includes a loudspeaker 3a and a display 3b. The loudspeaker 3a may generate artificial speech or symbolic sound tracks, and the display 3b may convey text, images, icons or other symbols.

Preferably, the audiovisual unit 3 is located in close vicinity to the inlet area 4 of the sensor unit 5, in order to direct the person's 12 attention to this area. It is capable of calling for the immediate attention of the person 12 upon presence registration or at some later instant. It is also capable of conveying an instruction, even a detailed one, in the case that the person 12 may need one.

The location of the audiovisual unit 3 in close vicinity to the inlet area 4 is particularly important in the case of an experienced but distracted or otherwise un-attentive person 12. When reminded by the signals from the audiovisual unit 3, the experienced person 12 will react with minimal time delay, and deliver a directed breath towards the inlet area 3. Alternative solutions would increase the mental load of the person 12.

From research in experimental psychology it is known that the reaction time of a person may vary from 0.2 to several seconds depending on the degree of distraction, mental load, and choice options. The capability of the present invention to both call for and direct the attention of the experienced person 12 to the sensor inlet area is thus highly important in order to save time.

As a consequence of mixing between ambient and expiratory air, the signal generated by the sensor element 8 will be diminished by a factor corresponding to the dilution of the expiratory air. Therefore, another sensor element 7 is included in addition to the element 8, for measuring the concentration of a tracer gas, e.g. carbon dioxide ($CO_2$) or water vapor. Since the tracer gas concentration is approximately constant when leaving the airways on expiration, it is possible to obtain a fair approximation of the degree of dilution of the air entering the sensor unit 5. Another option for a tracer signal besides $CO_2$ and $H_2O$ is temperature. The temperature of expiratory air is almost the same as body temperature as it leaves the mouth or nose but is cooled will get closer to ambient upon mixing.

The sensor elements 7 and 8 constitute the receiver ends of a measurement cell for infrared (IR) transmission measurement. From an infrared emitter 6, preferably a blackbody radiating element, a beam of broadband infrared radiation is illuminating the cell, and eventually after multiple reflections it will reach the elements 7, and 8. Preferably, the emitter 6 is modulated at a frequency, e.g. 5 Hz, above the frequency band of typical signals. Each of the sensor elements 7 and 8 include thermopile detectors of infrared radiation with bandpass interference filters tuned to the absorption peak of the substance to be detected. The element 8 includes a filter with the pass band within the interval 9.1 . . . 9.9 μm for ethyl alcohol, and the element 7 the filter in the interval 4.2 . . . 4.3 μm in the case of $CO_2$ as tracer gas. Water vapor, an alternative tracer gas, has strong absorption in the wavelength intervals 2.5 . . . 2.8 μm and 5.7 . . . 6.9 μm. Other combinations of gases and filter characteristics are possible. Acetone, acetaldehyde, methyl alcohol, carbon monoxide, methane, ethane, propane, pentane, hexane, heptane, octane, isoprene, ammonia, hydrogen sulfide, methyl mercaptan, ethyl acetate, dimethyl ether, diethyl ether, benzene, toluene, methyl ethyl ketone, and methyl isobutyl ketone are examples of volatile substances that may be of interest from a diagnostic or toxicological perspective.

The optical path from the IR emitter 6 to the detectors 7, and 8 may depend on the concentration range and the absorption coefficients of the actual substances. $CO_2$ has strong absorption and high concentration in expiratory air which calls for a short optical path, 10-25 mm. For alcohol detection below the legal concentration limits, path lengths of more than 0.5 m may be necessary. By folding the optical path using multiple reflections, the length/width/height of the sensor unit 5 can still be kept smaller than 70/30/15 mm.

The sensor unit 5 responds almost instantaneously, i.e. within a fraction of a second, to concentration variations occurring at the inlet area 4. This is partly due to the small distance between the inlet area 4 and the sensor unit 5, typically 10-20 mm, its small inner volume, typically 20-60 ml, and the air volume flow, typically 100-200 ml/sec, generated by the fan 9. It is also due to the relatively fast modulation frequency of the infrared emitter. The signal information extracted from the sensor elements 7 and 8 is represented as the amplitude of the modulation frequency.

The signals from the sensor elements 7, 8 are brought to an analyzer 10, which preferably includes a general purpose digital microcontroller with capacity to execute signal algorithms, and also controlling the audiovisual unit 3, IR emitter 6, fan or pump 9. Signal conversion between different formats, including analog signals, can be managed by the microcontroller 10, which will also be capable of communicating with external units, e.g. an actuator unit for taking action or counteraction depending on the result of the breath test. Electric power for the system 1 can either be obtained from a battery or from an external power source. The system 1 can be designed as a stand-alone unit, or as an integrated part of other inventories, e.g. a vehicle compartment or entrance of building or workplace. Preferably, the inlet area 4 includes means for protection of the sensor unit 5, e.g. a lid which is closed when the system 1 is inactive.

In order to meet requirements on electromagnetic emission and immunity, the system according to the invention includes capacitive and inductive electronic elements for protective purposes. In addition, the elements 7 and 8 and their associated analog input stages are preferably equipped with differential preamplifiers in order to suppress the influence of common mode interference.

The system according to the invention is preferably confined in a box to be wall-mounted in such a way that the means for registration 2, audiovisual unit 3, and inlet area 4, are located on one side of the box and thereby accessible through a hole in the wall.

Figure 2:
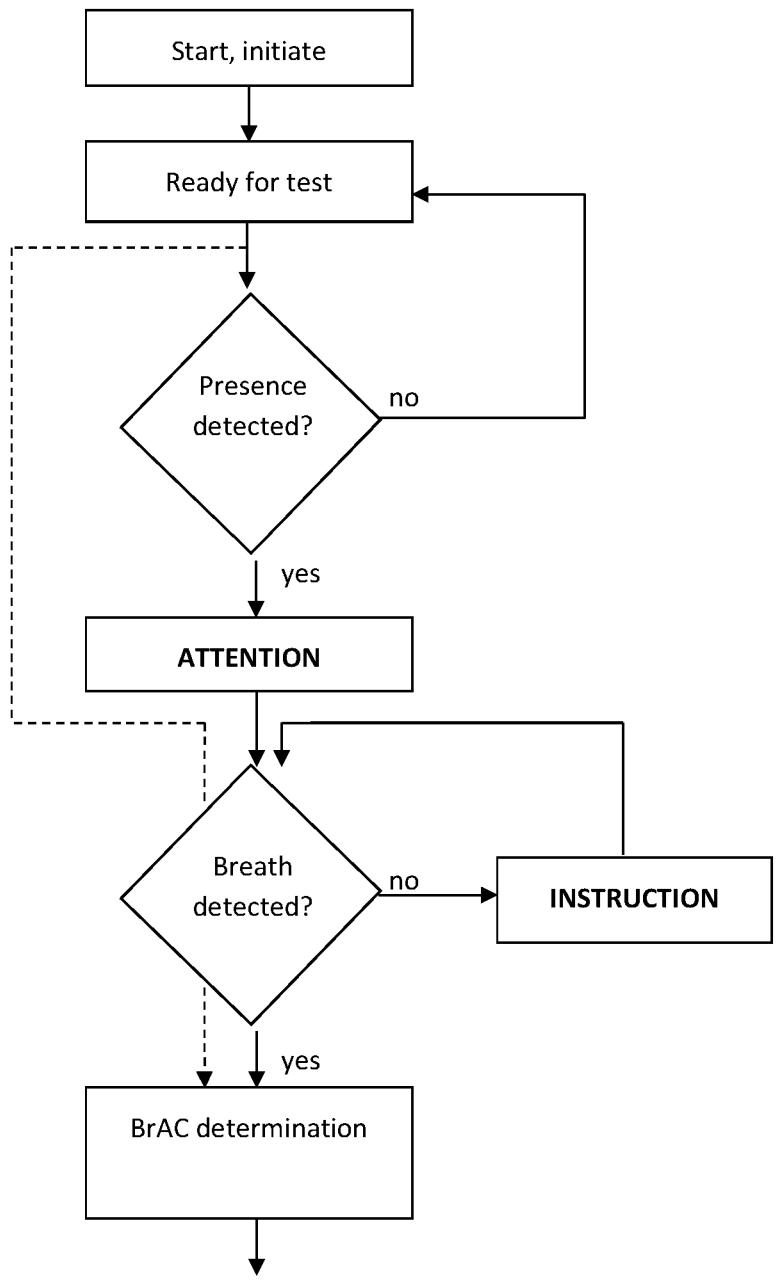
FIG. 2 shows a flow graph of the system function.

FIG. 2 shows a flow diagram of the system function according to the invention. The system is started or initiated either manually or automatically, by some external control signal. In the case of a vehicle, the start signal could be unlocking of the vehicle doors. The initiating phase preferably involves some self-testing functions of the system, to make sure that no functional errors have occurred since the previous test occasion. The initiating phase could also include preheating of sensitive components and stabilization of signals.

When the system is ready for test it will remain in a standby condition until the presence of a person within the predefined position is detected. As previously described, detection may or may not involve identification of the person, and could require two-way communication between the person and the system. After or during the presence detection step, the system will call for the person's attention by coordinated flashing light, distinctive and directional sound combined with specific symbol or icon representing the breath test.

An experienced person is then expected to direct expiratory air towards the sensor inlet area, whereas an inexperienced person may require a more or less detailed instruction on how to proceed. Example of instruction provided verbally or as a text message: "Take a deep breath, lean over, open your mouth wide and exhale gently." Alternatively, instructions are provided by text, still or moving images, graphic symbols or other means. If the criteria for breath detection are not fulfilled after one round of instruction, repeated instructions may be delivered at increasing level of detail.

The criteria for breath detection preferably involve tracer gas detection as previously described. In the case of $CO_2$ as tracer gas, a simple criterion is reaching a threshold $CO_2$ concentration of e.g. 2500 ppm (parts per million), which corresponds to a dilution factor of 20 (alveolar $CO_2$ concentration being approximately 5 vol %, or 50 000 ppm). Additional criteria could be related to the time derivative of the $CO_2$ signal. The simultaneously measured alcohol concentration will in this case have to be multiplied with 20 in order to obtain an estimated breath alcohol concentration. The criteria for breath detection should also include correction for background $CO_2$ concentration, which is typically 400-600 ppm in normal environments. A mathematical expression or algorithm will normally be adequate for defining the criteria, using settable parameters to adapt for variations between different conditions. Such an algorithm can be implemented for execution in real time using standard microcontrollers.

The level of dilution is a measure of the signal quality. High concentration (small dilution factor) provides high confidence of the determination, whereas the influence of interfering factors, such as other nearby persons, will increase with degree of dilution. Preferably, the result of the breath test is presented not only as a concentration but also in terms of an estimated error depending on the dilution factor.

Breath detection may in some applications override the presence detection as symbolized in FIG. 2 by the dotted line short-cutting both the 'attention' and 'instruction' sequences. Another way of expression is to include the tracer gas detection into the 'means of registration'.

Determination of BrAC is performed by another algorithm based on the correlation between the signals from the sensor elements 7 and 8. When the sensor unit 5 is receiving expired air from a person, both sensor elements exhibit concentration peaks which occur almost simultaneously. An average BrAC value is obtained by multiplying a number of measured alcohol concentrations by their respective dilution factors. By averaging, the effect of noise and interference is reduced. A small time difference between the $CO_2$ and the alcohol signals due to differences caused by the anatomic dead space or by the design of the sensor unit 5 is also possible to accommodate in the algorithm.

The completion and result of a breath test defined by fulfillment of the criteria for breath detection, is preferably communicated to the person, e.g. using the audiovisual unit 3.

In the flow diagram of FIG. 2, the further steps taken after termination of the actual breath test are not included, since they may be highly depending on the actual application of the breath test. Such steps may involve rule-based decision for controlling action or counteraction based on the determination, e.g. enable/disable functions of a vehicle or locking/unlocking of door.

Figure 3A:
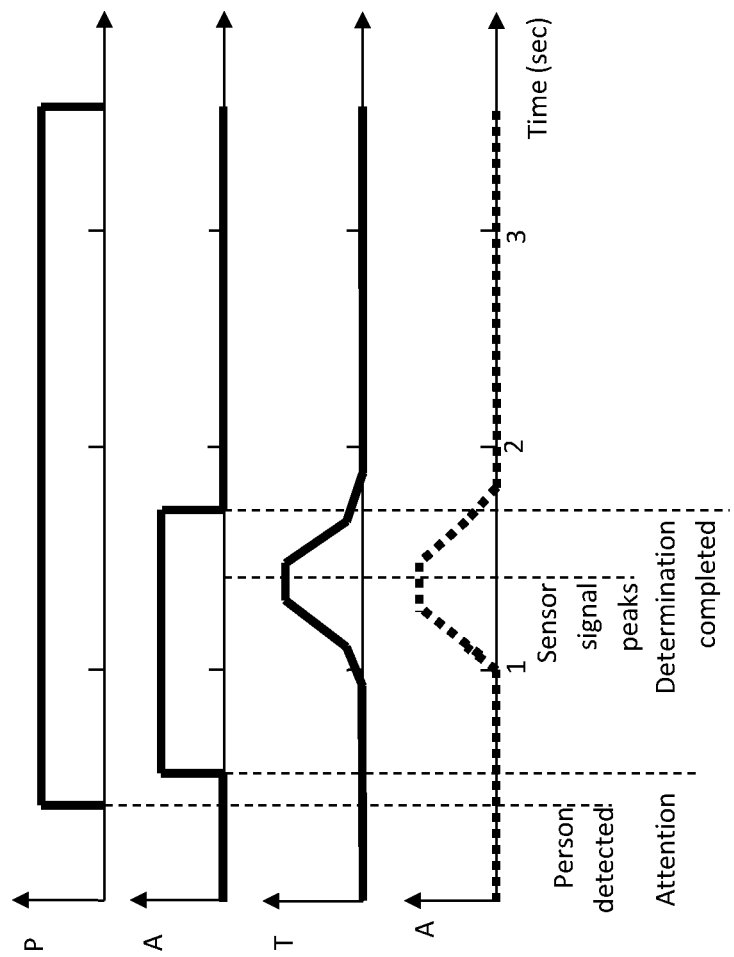
FIG. 3a shows a time sequence of typical breath tests performed with the system according to the invention for an experienced person.
Figure 3B:
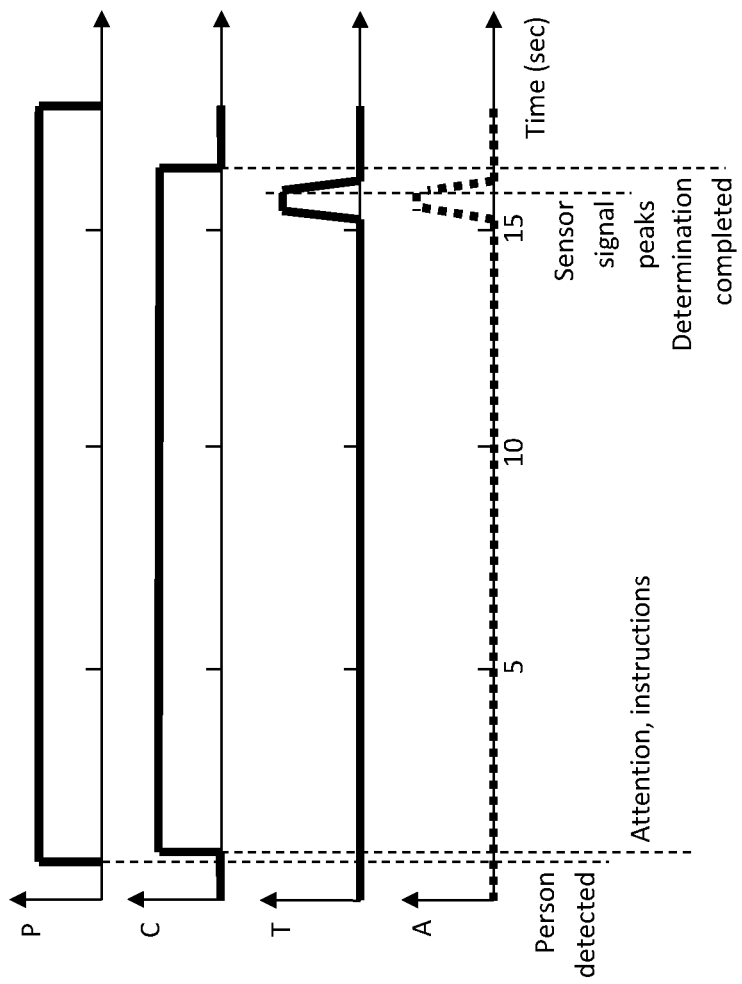
FIG. 3b shows a time sequence of typical breath tests performed with the system according to the invention for an inexperienced person.

FIG. 3 shows time sequences of typical breath tests performed with the system according to the invention for (a) and experienced person, and (b) an inexperienced person. From top to bottom the signals represented are: 'P' presence, 'C' communication, 'T' tracer gas, 'A' alcohol in both diagrams 3(*a*) and 3(*b*).

In the time sequence of FIG. 3(*a*) a person is detected within the first half second, and is almost immediately followed by the 'attention' communication to the experienced test person, who responds after another half a second by distinctive peaks representing both the tracer substance and alcohol. After two seconds, the breath test is completed.

The time sequence of FIG. 3(*b*) follows a somewhat different pattern. The inexperienced test person does not immediately respond, but requires a short instruction before supplying an approved breath. The entire sequence is completed after 15 seconds.

The invention claimed is:

1. A breath test system for determining the concentration of a volatile substance present in a breath of air, said breath test system comprising:
    a chamber having an inlet for receiving a breath of air, an outlet, and a lumen extending between said inlet and said outlet;
    an electromagnetic emitter configured to emit light into said lumen of said chamber;

at least one electromagnetic detector configured to detect light emitted by said electromagnetic emitter after said light has passed through said lumen, said at least one electromagnetic detector being configured to generate a signal corresponding to at least one characteristic of said light after said light has passed through said lumen and been received by said at least one electromagnetic detector;

said light emitted by said electromagnetic emitter and detected by said at least one electromagnetic detector being directed along an optical path contained within said lumen of said chamber, said optical path including a plurality of reflections occurring between the side walls of the chamber so that the optical path is located within the lumen of said chamber, whereby to increase the length of said optical path within said lumen of said chamber and thereby increase the contact time of the light with a breath of air located within said lumen of said chamber;

apparatus configured to:
  (i) monitor a vehicle for the presence of an external control signal, and if the external control signal is present, initiate an initiating phase which preheats at least one of the chamber, the electromagnetic emitter, and the at least one electromagnetic detector;
  (ii) register the presence of a person in the vicinity of said inlet;
  (iii) call for and direct the immediate attention of the person in the vicinity of said inlet; and
  (iv) provide instructions to a person in the vicinity of said inlet to direct a breath of air into said inlet such that the breath of air enters the lumen of said chamber; and an analyzer for analyzing the signal generated by the at least one electromagnetic detector so as to determine (i) whether a breath of air has entered said lumen of said chamber; and (ii) if a breath of air has entered said lumen of said chamber, the concentration of the volatile substance present in a breath of air.

2. The breath test system according to claim 1, wherein said breath test system comprises a first electromagnetic detector providing a first signal corresponding to the concentration of the volatile substance within the breath of air and a second electromagnetic detector providing a second signal corresponding to the concentration of a tracer substance within the breath of air, said determination of the concentration of the volatile substance present in the breath of air taking said tracer substance concentration into account.

3. The breath test system according to claim 2, wherein said first electromagnetic detector and said second electromagnetic detector are based on substance-specific infrared absorption in predetermined wavelength bands.

4. The breath test system according to claim 1, wherein the volatile substance is acetone, acetaldehyde, methanol, ethanol, carbon monoxide, methane, ethane, propane, pentane, hexane, heptane, octane, isoprene, ammonia, hydrogen sulfide, methyl mercaptan, ethyl acetate, dimethyl ether, diethyl ether, benzene, toluene, methylethyl ketone, or methyl isobutyl ketone or a combination thereof.

5. The breath test system according to claim 1, wherein a response time of said breath test system is shorter than one second.

6. The breath test system according to claim 1, wherein said apparatus for registering the presence of a person providing the breath of air comprises a microphone and means for identification of the person using voice recognition, and further wherein said apparatus further comprises a camera or other optical detector, and means for identification of the person providing the breath of air using image analysis, bar code reading or biometrics.

7. The breath test system according to claim 1, comprising means for active transport of air from said inlet to said at least one electromagnetic detector and said outlet.

8. The breath test system according to claim 1, wherein the immediate attention of the person is called for by coordinated flashing of a light, and a distinctive sound combined with a specific symbol or icon representing said breath test.

9. The breath test system according to claim 1, wherein said instructions are provided to the person verbally or as text message, step-by-step and with the level of detail provided to the person increasing with time.

10. The breath test system according to claim 1, wherein said breath test system further comprises a display for communicating messages of text, symbols, icons or images, or a loudspeaker for communicating recorded spoken messages or symbolic sound tracks.

11. The breath test system according to claim 1, wherein said determination also depends on quality criteria, and wherein said quality criteria includes at least one of: concentration of tracer gas exceeding a predefined threshold, or background variations of said signal being below a predefined upper limit.

12. The breath test system according to claim 1, wherein said system is integrated into an interior of the vehicle.

13. The breath test system according to claim 1, wherein the total test time of said breath test system does not exceed five seconds.

14. The breath system according to claim 1 further comprising capacitive and inductive electronic elements for protective purposes, and wherein the at least one electromagnetic detector and associated analog input stages is equipped with differential preamplifiers in order to suppress the influence of common mode interference.

15. The breath test system according to claim 1, wherein said breath test system is confined in a box adapted to be wall-mounted in such a way that said apparatus for registering the presence of the person and said inlet are located on one side of the box and thereby accessible through a hole in the wall to which said breath test system is mounted.

16. The breath test system according to claim 1, wherein said external control signal comprises unlocking of the vehicle doors.

17. The breath test system according to claim 1, wherein said apparatus comprises a seat for receiving a person in the vicinity of said inlet, and a force sensor for registering the presence of a person disposed in said seat, whereby to register the presence of a person in the vicinity of said inlet.

* * * * *